(12) United States Patent
Li et al.

(10) Patent No.: US 10,983,119 B2
(45) Date of Patent: Apr. 20, 2021

(54) DEVICE FOR RAPID DIAGNOSTIC TESTS TO DETECT ANTIGENS WITH IMPROVED SENSITIVITY

(71) Applicants: General Electric Company, Schenectady, NY (US); TOKITAE LLC, Bellevue, WA (US)

(72) Inventors: Bing Li, Clifton park, NY (US); Matthew Jeremiah Misner, Delanson, NY (US); David Roger Moore, Schenectady, NY (US); Kevin Paul Flood Nichols, Issaquah, WA (US); David Cate, Bellevue, WA (US); Matthew F Rosen, Cambridge, MA (US)

(73) Assignees: GENERAL ELECTRIC COMPANY, Schenectady, NY (US); TOKITAE LLC, Bellevue, WA (US)

( * ) Notice: Subject to any disclaimer, the term of this patent is extended or adjusted under 35 U.S.C. 154(b) by 387 days.

(21) Appl. No.: 15/401,333

(22) Filed: Jan. 9, 2017

(65) Prior Publication Data
US 2017/0212108 A1     Jul. 27, 2017

Related U.S. Application Data

(63) Continuation-in-part of application No. 15/005,054, filed on Jan. 25, 2016.

(51) Int. Cl.
    *G01N 33/558*     (2006.01)
    *G01N 33/543*     (2006.01)

(52) U.S. Cl.
    CPC ..... *G01N 33/558* (2013.01); *G01N 33/54386* (2013.01)

(58) Field of Classification Search
    CPC .............. G01N 33/558; G01N 33/54386
    See application file for complete search history.

(56) References Cited

U.S. PATENT DOCUMENTS 5,382,515 A * 1/1995 Shah .................. C07K 14/47
                                                     435/17
5,384,264 A * 1/1995 Chen .................. B01L 3/5023
                                                     422/400

(Continued)

FOREIGN PATENT DOCUMENTS

WO    WO-2010099607 A1 * 9/2010 ........... G01N 33/569

OTHER PUBLICATIONS

Laderman et al. "Rapid, Sensitive, and Specific Lateral-Flow Immunochromatographic Point-of-Care Device for Detection of Herpes Simplex Virus Type 2-Specific Immunoglobulin G Antibodies in Serum and Whole Blood" Clinical and Vaccine Immunology, 2008, pp. 159-163 (Year: 2008).*

(Continued)

*Primary Examiner* — Christine Foster
(74) *Attorney, Agent, or Firm* — Fletcher Yoder, P.C.

(57) ABSTRACT

A rapid diagnostic testing device for testing of a biological sample is provided. The device comprises a channeled construct, at least one lateral flow unit, and a cassette housing. The channeled construct is configured to receive a biological sample to form at least partially purified biological sample. The lateral flow unit is at least partially disposed in the cassette housing. The lateral flow unit comprises: a sample receiving zone, a conjugate zone and a detection zone. The sample receiving zone is operatively coupled to the channeled construct for receiving the partially purified biological sample comprising at least one analyte. The conjugate zone comprising a conjugate particle to bind the analyte is disposed adjacent to the first side of the sample receiving zone. The detection zone is disposed adjacent to (Continued)

the second side of the sample receiving zone and comprises at least one binding agent for detecting the analyte.

22 Claims, 11 Drawing Sheets

(56) References Cited

U.S. PATENT DOCUMENTS

| | | | | |
|---|---|---|---|---|
| 5,559,041 | A * | 9/1996 | Kang | G01N 33/54366 422/400 |
| 6,008,059 | A * | 12/1999 | Schrier | G01N 33/5002 422/412 |
| 6,737,277 | B1 * | 5/2004 | Kang | G01N 33/54366 422/401 |
| 7,109,023 | B2 * | 9/2006 | Kang | G01N 33/54386 422/537 |
| 8,535,617 | B2 | 9/2013 | MacDonald et al. | |
| 8,859,265 | B2 | 10/2014 | Bae et al. | |
| 9,121,857 | B2 | 9/2015 | Grebe | |
| 9,651,508 | B2 | 5/2017 | Bischof et al. | |
| 2003/0049167 | A1 * | 3/2003 | Jerome | G01N 21/8483 422/420 |
| 2004/0248322 | A1 * | 12/2004 | Charlton | G01N 33/558 436/518 |
| 2006/0128029 | A1 * | 6/2006 | Goerlach-Graw | G01N 33/558 436/514 |
| 2007/0020768 | A1 * | 1/2007 | Rundstrom | G01N 33/543 436/514 |
| 2009/0053731 | A1 * | 2/2009 | Sojka | G01N 33/57476 435/7.1 |
| 2009/0286692 | A1 * | 11/2009 | Wainwright | B01L 3/502723 506/9 |
| 2012/0024788 | A1 * | 2/2012 | Kelso | B01L 3/5023 210/651 |
| 2013/0022969 | A1 | 1/2013 | Kim et al. | |
| 2013/0112612 | A1 | 5/2013 | Blankenstein et al. | |
| 2016/0169879 | A1 * | 6/2016 | Snider | G01N 33/558 435/287.2 |
| 2016/0169882 | A1 * | 6/2016 | Snider | A61B 90/98 435/287.2 |
| 2017/0212112 | A1 * | 7/2017 | Li | G01N 33/56905 |

OTHER PUBLICATIONS

Michael A. Mansfield, "The Use of Nitrocellulose Membranes in Lateral-Flow Assays", Forensic Science and Medicine, Drugs of Abuse, pp. 71-85, 2005.
Thomas C. Tisone, "In-line processing trends for lateral-flow immunoassay manufacturing", IVD technology, Jun. 1, 2007; 7 pages.

* cited by examiner

DEVICE FOR RAPID DIAGNOSTIC TESTS TO DETECT ANTIGENS WITH IMPROVED SENSITIVITY

CROSS REFERENCE TO RELATED APPLICATIONS

This application is a continuation in part claims the benefit of U.S. application Ser. No. 15/005,054, titled "Integration of sample separation with diagnostic tests for improved sensitivity", filed on Jan. 25, 2016, which is incorporated herein by reference.

FIELD

This application relates generally to an improvement in currently available rapid diagnostic tests (RDTs), particularly RDTs for malaria. In a particular aspect, the application relates to a device for rapid diagnostic testing of a blood sample.

BACKGROUND

A rapid diagnostic test (RDT) is a medical diagnostic test that is less time consuming and less labor intensive. RDTs are suitable for preliminary and/or emergency medical screening, for example, for use in medical facilities with limited resources, and offer a useful alternative to microscopy in situations where reliable microscopic diagnosis facility is not available or is not immediately available. RDTs also allow point-of-care (POC) testing in primary care. RDTs do not require clinical diagnostic methods, such as enzyme-linked immunosorbent assay (ELISA) or polymerase chain reaction (PCR). RDTs can be performed independent of laboratory equipment by minimally trained personnel, and deliver instant results. RDTs provide results within two hours, and typically provide results in approximately 30 minutes.

An RDT employs a dipstick or cassette format for testing a biological specimen, such as a blood sample. For testing, the biological specimen collected from a patient is applied to a sample pad on a test strip (or card) of the RDT dipstick or cassette along with certain reagents. Depending on the type of test that is being conducted, after a determined period of time, presence or absence of specific bands in a test strip window indicates whether a certain antigen of interest is present in the biological specimen, such as a patient's sample. Generally, a drop of the biological specimen is added to the RDT device through a sample well, and then a buffer is usually added through a buffer well. The buffer carries the biological specimen along the length of the RDT device.

In the currently marketed RDTs for malaria, hemoglobin present in red blood cells typically causes background noise while using a nitrocellulose-based detection pad. This in turn affects the detection performance or sensitivity of the RDT assay kit. In addition, the currently marketed RDT devices for malaria utilize only about 5 μL of a blood sample while a finger prick can generate up to 500 μL of sample. The small volume of sample affects detection, particularly if the level of analyte in the sample is low and can lead to false negative test results.

In general, the methods disclosed in the art for removal of red blood cells from whole blood employs agents that lysed cells, induce affinity binding, or agglutination of cells. Disadvantages of the methods disclosed in the art include a greater number of steps required for the assay and/or the increased cost of reagents/materials required for the assays. There is a need for improving sensitivity of RDTs, particularly the sensitivity of RDTs for malaria detection while retaining the lower cost of such tests.

BRIEF DESCRIPTION

In one embodiment, a rapid diagnostic testing device for rapid diagnostic testing of a biological sample is provided. The device comprises a channeled construct configured to receive at least a portion of the biological sample for rapid separation of one or more undesired components from the biological sample and forms at least partially purified biological sample; at least one lateral flow unit is operatively coupled to the channeled construct, and a cassette housing comprising a sample well, a plurality of rib structure, a first surface and a second surface, wherein the lateral flow unit is at least partially disposed in the cassette housing. The lateral flow unit comprises: a sample receiving zone operatively coupled to the channeled construct for receiving the partially purified biological sample from the channeled construct, wherein the partially purified biological sample comprises at least one analyte, and wherein the sample receiving zone comprises a first side and a second side; a conjugate zone adjacent to the first side of the sample receiving zone, wherein the conjugate zone comprises a conjugate particle for binding with the analyte; and a detection zone adjacent to the second side of the sample receiving zone, wherein the detection zone comprises at least one binding agent for detecting the analyte by capturing the analyte.

In one embodiment, a diagnostic testing device for rapid diagnostic testing of a blood sample is provided. The device comprises a channeled construct configured to receive at least a portion of the blood sample for rapid separation of blood cells and plasma from the blood sample; at least one lateral flow unit operatively coupled to the channeled construct; and a cassette housing comprising a sample well, a plurality of rib structure, a first surface and a second surface, wherein the lateral flow unit is at least partially disposed in the cassette housing. The lateral flow unit comprises: a sample receiving zone operatively coupled to the channeled construct for receiving at least a portion of the plasma from the channeled construct, wherein the plasma comprises at least one analyte, and wherein the sample receiving zone comprises a first side and a second side; a conjugate zone disposed adjacent to the first side of the sample receiving zone, wherein the conjugate zone comprises a conjugate particle for binding with the analyte to form an analyte-conjugate complex; and a detection zone disposed adjacent to the second side of the sample receiving zone, wherein the detection zone comprises at least one binding agent for detecting the analyte by capturing the analyte.

In another embodiment, a diagnostic testing device for rapid diagnostic testing of a blood sample is provided herein. The device comprises a channeled construct configured to receive at least a portion of the blood sample for rapid separation of blood cells and plasma from the blood sample; at least one lateral flow unit operatively coupled to the channeled construct, wherein the channeled construct is vertically disposed relative to the lateral flow unit, and a cassette housing comprising a sample well and a plurality of rib structure; wherein the lateral flow unit is at least partially disposed in the cassette housing. The lateral flow unit comprises: a sample receiving zone operatively coupled to the channeled construct for receiving at least a portion of the plasma from the channeled construct, wherein the portion of the plasma comprises at least one antigen, and wherein the sample receiving zone comprises a first side and a second side, a conjugate zone disposed adjacent to the first side of the sample receiving zone, wherein the conjugate zone comprises an antibody for binding with the antigen to form an antigen-antibody complex; and a detection zone disposed adjacent to the second side of the sample receiving zone, wherein the detection zone comprises a test region comprising a secondary antibody disposed on the test region for detecting the antigen by capturing the antigen-antibody complex.

DRAWINGS

These and other features, aspects, and advantages of the present invention will become better understood when the following detailed description is read with reference to the accompanying drawings in which like characters represent like parts throughout the drawings, wherein.

DETAILED DESCRIPTION

Figure 1:
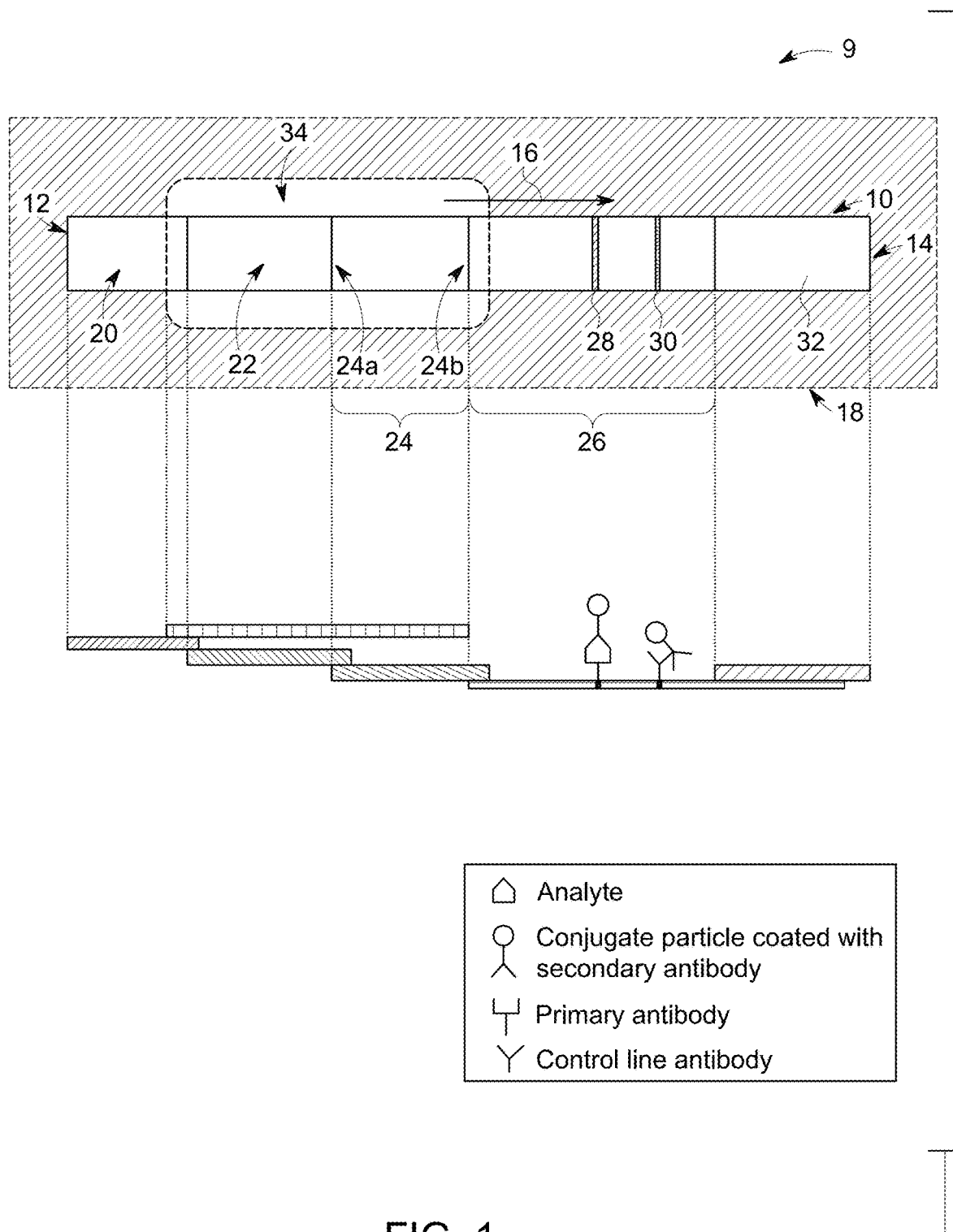
FIG. 1 is a schematic drawing of a top view of one embodiment of an RDT device.

Rapid diagnostic tests (RDTs) or rapid diagnostic testing devices (RDT devices) broadly include lateral flow assays (LFAs) and/or flow through assays (FTAs). RDTs or RDT device using LFAs are provided herein, wherein the LFAs are used for detection of analytes, such as different biomarkers present in a blood sample by immuno-chromatographic antigen-detection tests. The immuno-chromatographic antigen-detection tests rely on capture of analytes (antigens) by dye-labeled antibodies to produce a visible band on a lateral flow assay unit, such as a nitrocellulose test strip. The lateral flow assay unit is encased in a housing, referred to as a cassette. For RDTs, in one aspect, the dye-labeled antibody or conjugate particle-coupled antibody binds to an analyte (antigen) such as a malarial biomarker. The resultant analyte-antibody complex is further captured by the binding agents (secondary antibody) on a test line of the lateral flow unit, forming a visible test line in a result window of the RDT device. In another aspect, the analytes bind to the antibodies on the test line forming analyte-antibody complex, which is further bound to conjugate particle-coupled antibody on the test line, forming a visible test line in the result window. In this case, a positive result is indicated by the presence of a test line. Presence of excess conjugate particles is desired, so that during detection, some of the conjugate particles are captured at the test line and continue to flow towards the second line of immobilized antibodies to a control line. This control line typically comprises a species-specific anti-immunoglobulin antibody, specific for the conjugate particle-coupled antibody. The control line gives information on integrity of the conjugate particle-coupled antibody and fluidics of the lateral flow unit.

To more clearly and concisely describe the subject matter of the disclosed application, the following definitions are provided for specific terms, which are used in the following description and the appended embodiments. Throughout the specification, exemplification of specific terms should be considered as non-limiting examples.

The singular forms "a", "an" and "the" include plural referents unless the context clearly dictates otherwise.

Approximating language, as used herein throughout the specification and claims, may be applied to modify any quantitative representation that could permissibly vary without resulting in a change in the basic function to which it is related. Accordingly, a value modified by a term such as "about" is not to be limited to the precise value specified. In some instances, the approximating language may correspond to the precision of an instrument for measuring the value. Where necessary, ranges have been supplied, and those ranges are inclusive of all sub-ranges there between.

As used herein, the term "rapid diagnostic test" (RDT) refers to testing of a biological sample, which can be carried out at the point of care to obtain a fast diagnosis. A RDT is a medical diagnostic test that is quick and easy to perform and can be carried out even in the absence of laboratory techniques such as microscopy, enzyme-linked immunosorbent assay (ELISA) or polymerase chain reaction (PCR). RDTs provide results within two hours, typically in approximately 30 minutes. By way of a non-limiting example, RDTs for malaria typically require about 30 minutes from the time of sample collection to the time of obtaining a result. It will be understood that the time required for an RDT depends on variables such as the type of sample, the amount of sample, the nature of the analyte and the like.

As used herein, the term "channeled construct" refers to a structure having pores, a first surface and a second surface. The first surface of the channeled construct is present at the top and second surface of the channeled construct present at the bottom of the channeled construct, when the channeled construct is vertically disposed on a lateral flow unit. A cross-section of the channeled construct may be larger at the first surface and relatively smaller at the second surface. The channeled construct may expand in more than one directions. By way of example, two or more separation elements may join to form a single unit of channeled construct. In a non-limiting example, the channeled construct may be in the shape of the letter "L."

Embodiments of a rapid diagnostic testing (RDT) device for testing of a biological sample is provided herein. The RDT device is compatible with equipment-free, point of care (POC) analyte-separation and detection process. For example, the RDT device provides rapid diagnostic testing by immunochromatographic separation and detection.

According to embodiments of the present technique, the RDT device comprises a channeled construct, at least one lateral flow unit, and a cassette housing. The channeled construct is configured to receive at least a portion of a biological sample for rapid separation of undesired materials from the biological sample and forms at least partially purified biological sample. The lateral flow unit comprises a sample receiving zone, a conjugate zone, and a detection zone. The sample receiving zone comprises a first side and a second side. Further, the sample receiving zone is operatively coupled to the channeled construct for receiving the partially purified biological sample from the channeled construct. The partially purified biological sample comprises at least one analyte. The conjugate zone is disposed adjacent to the first side of the sample receiving zone, wherein the conjugate zone comprises a conjugate particle for binding with the at least one analyte. The detection zone is disposed adjacent to the second side of the sample receiving zone. The detection zone comprises at least one binding agent for detecting the at least one analyte by capturing the analyte. The cassette housing comprises a sample well, a plurality of rib structures, a first surface and a second surface. The lateral flow unit is operatively coupled to the channeled construct. Further, the lateral flow unit is at least partially disposed in the cassette housing.

As noted, the lateral flow unit and the channeled construct are operatively coupled to each other, wherein the term "operatively coupled" refers that the channeled construct and the lateral flow unit are coupled or connected when the RDT device is in operation. The channeled construct and the lateral flow unit are coupled or connected at least by a fluidic communication. The fluidic communication may include at least a fluid flow from the channeled construct to the lateral flow unit during operation of the device. For example, a plasma derived from the blood sample flows from the channeled construct to the lateral flow unit, which provides a fluidic communication under the operating conditions of the diagnostic testing device. In some embodiments, the channeled construct and the lateral flow unit may be in a physical contact.

The biological sample is a sample of blood, feces, sweat, saliva, mucous, milk, urine, semen, serum, plasma, sputum, tears, vaginal fluid, or tissue. In some embodiments, the RDT device is employed for testing of a blood sample. The RDT device is configured to separate blood cells from a blood sample to derive a plasma. Further, the plasma derived from the blood sample is used for detection of analytes using the RDT device.

The channeled construct of the RDT device is disposed vertically relative to the at least one lateral flow unit. The term "vertically disposed relative to the lateral flow unit" means that the channeled construct is placed in a plane that is different from the plane comprising the lateral flow unit, and one of these planes is vertically disposed on the other. In some embodiments, an angle between the plane where channeled construct is placed and the plane comprising the lateral flow unit may vary between 30° and 120°. In some embodiments, the channeled construct is disposed vertically, at a right-angle (90°) relative to the lateral flow unit. In such embodiments, the channeled construct is disposed at a right-angle on the sample window of the cassette housing of the RDT device. The plasma of the blood sample is transferred to the sample window from the channeled construct, where the channeled construct provides an initial separation of the blood sample by a physical separation, for example, size exclusion.

The lateral flow unit as employed for the present diagnostic testing device is a unit where liquid flows across the length of the lateral flow unit or lateral flow strip. The terms "lateral flow unit," or "lateral flow assay strip" may be used interchangeably throughout the specification. Traditionally designed lateral flow units are composed of a variety of materials, each serving one or more purposes, overlapping onto one another, mounted on a backing substrate (e.g. backing card) using a pressure-sensitive adhesive.

FIG. 1 illustrates an example of an RDT device 9 of the present specification. The RDT device 9 is configured to rapidly detect analytes present in a biological sample. The RDT device 9 comprises a lateral flow unit 10 and a channeled construct 34. The lateral flow unit 10 is configured to receive plasma derived from the blood sample. The lateral flow unit 10 comprises a buffer reservoir 20, a conjugate zone 22, a sample receiving zone 24, and a detection zone 26. In some embodiments, the one or more zones of the lateral flow unit 10 may be made of different materials. In some other embodiments, the various zones of the lateral flow unit 10 is made of a single material.

In certain embodiments, the sample receiving zone of the lateral flow unit is operatively coupled to the channeled construct for receiving one or more components of the biological sample. The one or more components received by the channeled construct may include an analyte of interest, which may be subsequently detected by the lateral flow unit. In embodiments where the biological sample is a blood sample, the sample receiving zone is configured to receive at least a portion of a plasma of the blood sample from the channeled construct, where the blood sample comprises at least one analyte.

As illustrated in FIG. 1, one or more components of a biological sample, such as a plasma is received by the sample receiving zone 24, which may further be referred to as a "sample application pad" or a "sample pad." The sample receiving zone 24 has a first side 24a and a second side 24b. In one or more embodiments, the channeled construct 34 is vertically disposed on or adjacent to the sample receiving zone 24 such that the plasma from the channeled construct 34 is received by the sample receiving zone 24 of the lateral flow unit 10. The sample receiving zone 24 may be present on a fiber glass, quartz, or a cellulose substrate.

The conjugate zone of the lateral flow unit is disposed adjacent to the first side of the sample receiving zone, leaving enough distance between the conjugate zone and the detection zone of the lateral flow unit. The conjugate zone comprises one or more conjugate particles for binding with at least one analyte present in the biological sample.

Referring to FIG. 1, the conjugate zone 22 is disposed adjacent to the first side 24a of the sample receiving zone 24. The conjugate zone 22, may also be referred to as a "conjugate pad." In one embodiment, the conjugate zone 22 of the lateral flow unit 10 comprises a conjugate particle. In another embodiment, the conjugate zone 22 comprises a plurality of conjugate particles. In one or more embodiments, the number of conjugate particles present in the conjugate zone 22 may be greater than the number of analytes present in the sample. In the conjugate zone 22, a conjugate particle may be immobilized on the conjugate zone 22 of the lateral flow unit 10. The conjugate particle binds to the analyte of the plasma derived from the blood sample received by the lateral flow unit 10 or binds to binding agents disposed on the detection zone 26.

The conjugate particle may include colloidal gold, a colored particle, a fluorescent probe, a paramagnetic particle (such as paramagnetic monodisperse latex particle), or a combination thereof. The RDT device may further include alternative conjugate reporters such as cellulose nanobeads (CNB), magnetic beads, fluorescence tags, chemiluminescence molecules, or various shapes of gold nanoparticles including nanospheres, nanorods, nanoshells. All such alternative conjugate reporters are contemplated within the scope of embodiments presented herein. The conjugate particle is conjugated to one of the components of the biological sample, a component of the lateral flow assay strip (such as binding agent), a biomolecule such as a protein. The protein may be an antigen or an antibody, depending on a format of the assay.

The detection zone is disposed adjacent to the second side of the sample receiving zone. The detection zone comprises at least one binding agent for detecting the at least one analyte by capturing the analyte. The detection zone may be constructed on a nitrocellulose membrane. In one embodiment, the detection zone may be formed by depositing one or more binding agents on the nitrocellulose membrane.

Now referring to FIG. 1, the detection zone 26 is disposed adjacent to the second side 24b of the sample receiving zone 24. The analyte present in the plasma is detected in the detection zone 26 of the lateral flow strip 10. In some embodiments, the detection zone 26 comprises a test region 28. The test region 28 is a sub-zone of the detection zone 26 where binding agents are deposited. In some embodiments, the test region 28 is a test line on the lateral flow strip 10. The binding agents are typically proteins, such as antibodies or antigens, which serve to capture the analyte or the analyte-conjugate complex as they migrate to the test region 28, depending on the assay requirement. The detection zone further comprises a control region 30. In some embodiments, the test region 30 is a control line on the lateral flow strip 10. One or more binding agents having affinity towards the conjugate particles but no have affinity towards the analyte are deposited on the control region 30. In some embodiments, the binding agent is one or more of an antibody, or a labeled antibody. As used herein, "labeled antibody" includes any antibody coupled to an enzyme or a substrate, which is capable of changing color on exposure to a substrate, or reagent (such as an enzyme), respectively. As such, the antibody may be labeled with a dye, a metal particle (e.g., gold), a compound capable of producing chemiluminescence or fluorescence. In alternative embodiments, the antibody may be attached to a magnetic bead, a cellulose bead, a polymeric bead labeled with a dye, an affinity probe, and the like. In some embodiments, the binding agents are referred to as primary antibodies. In some alternative embodiments, the binding agents function as secondary antibodies.

In certain embodiments, the sample receiving zone 24 and the conjugate zone 22 of the lateral flow unit 10 are present on a common substrate. In such embodiments, the conjugate particle in the conjugate zone 22 may be present at one end of the common substrate and the sample receiving zone 24 may be present at the opposite end of the common substrate. In one embodiment, the common substrate further comprises a detection zone. In certain other embodiments, at least one of the sample receiving zone 24, the conjugate zone 22, and the detection zone 26 of the lateral flow unit 10 is constructed on a substrate that is different than a substrate on which the other zones are constructed. In one or more embodiments, the common substrate is selected from a glass fiber, a nitrocellulose, or a quartz. In one embodiment, the common substrate is a nitrocellulose membrane.

The lateral flow unit 10 further comprises a buffer reservoir 20 disposed adjacent to the conjugate zone 22. The buffer reservoir 20 is disposed such that when the RDT device 9 is in operation, the buffer added to the buffer reservoir 20 passes through the conjugate zone 22 of the lateral flow unit 10. In some embodiments, the buffer reservoir 20 is disposed on one end of the lateral flow unit 10. In one or more embodiments, a buffer solution may be added to the buffer reservoir 20. In some alternative embodiments, buffer reagents may be impregnated in the buffer reservoir 20, where the impregnated buffer reagents may be reconstituted as a buffer solution by adding water. The plasma sample comprising at least one analyte received by the sample receiving zone 24 is chased with the buffer from the buffer reservoir 20 to the different zones of the lateral flow unit 10. In operation, at least a portion of the buffer is passed from the conjugate zone 22 to the sample receiving zone 24, and subsequently to the detection zone 26 of the lateral flow unit 10. In one or more embodiments, the buffer reservoir comprises a non-lytic buffer. In some other embodiments, the buffer reservoir comprises a buffer with a surfactant concentration of less than about 0.01 mM.

In one or more embodiments, the lateral flow unit 10 further comprises a wicking pad or an absorbent pad 32. The wicking pad 32 is disposed adjacent to the detection zone 26. In some embodiments, the wicking pad 32 is disposed adjacent to the detection zone 26 and at the one end 14 of the lateral flow unit 10. The wicking force of the wicking pad 32 acts as a driving force to facilitate the buffer to flow through the lateral flow unit 10 along a direction represented by reference numeral 16. The wicking pad 32 draws the buffer to flow towards the wicking pad 32 based on the strong wicking force. When excess conjugate particles move past the test region 28 of the detection zone 26, the excess conjugate particles are entrapped in the wicking pad 32.

The RDT device may be operated in different ways, depending on the assay design, selection of conjugate particles, or selection of antibodies. In some embodiments, the conjugate zone 22 comprises conjugate particles which are coupled to a primary antibody. In some of these embodiments, when buffer laterally flows from the buffer reservoir 20 to the conjugate zone 22, the buffer remobilizes the dried primary antibody coupled-conjugate particles and subsequently flows to the sample receiving zone 24. Once the primary antibody-coupled conjugate particle and an analyte are in contact in the sample receiving zone 24, the primary antibody-coupled conjugate particle binds to the analyte to form a primary antibody-coupled conjugate-analyte complex.

The primary antibody-coupled conjugate-analyte complex along with remaining free conjugate particles and analyte particles may then migrate to the detection zone 26 of the lateral flow unit 10. The detection zone 26 is configured for detecting the analyte by capturing the primary antibody-coupled conjugate-analyte complex. In the detection zone 26, the binding agents, such as secondary antibodies disposed in the test region 28 interacts with the conjugate-analyte complex. The secondary antibody binds to the primary antibody, where the primary antibody is coupled to the conjugate particle of conjugate-analyte complex. On binding of the secondary antibody to the primary antibody-coupled conjugate-analyte complex, a signal is generated at the test region 28, which is typically measured for detection of analyte.

In some alternative embodiments, the conjugate zone 22 comprises conjugate particles which are coupled to secondary antibodies. In some of these embodiments, the test region 28 of the detection zone 26 comprises the binding agents that are primary antibodies specific to the analyte of interest. When buffer flows from the first end 12 to the second end 14 of the lateral flow unit 10, first, the analyte reaches the test region 28 of the detection zone 26 and is captured by the primary antibody disposed in the test region 28 and forms primary antibody-analyte complex. Secondly, the secondary antibody coupled-conjugate particles traverse along with the buffer and reach the test region 28 of the detection zone 26. The steps of capturing analyte by the primary antibody and traversing the secondary antibody coupled-conjugate particles along with the buffer from conjugate zone 22 to the detection zone 26 may occur simultaneously or consecutively. In the test region 28, once the secondary antibody coupled-conjugate particle is in contact with the primary antibody-analyte complex, the secondary antibody coupled-conjugate particle binds to the primary antibody-analyte complex. On binding of the secondary antibody coupled-conjugate particle to the primary antibody-analyte complex, a signal is generated at the test region, wherein presence of the signal is typically measured for detection of analyte.

The present RDT device of the subject specification advantageously allows for testing of larger volumes of samples compared to the sample used for currently available RDT devices. In some embodiments, a volume of blood sample employed for the present RDT device may be in a range from about 50 µL to about 200 µL. In some embodiments, a volume of the blood sample used for rapid diagnostic testing is in a range from about 75 µL to about 150 µL. In some other embodiments, a volume of the blood sample used for rapid diagnostic testing is in a range from about 90 µL to about 120 µL. The ability of an RDT device to process larger sample volume indicates that a larger volume of analyte reaches the lateral flow unit while using the present RDT device, which results in improving the signal intensity of the RDT device. In contrast, the sample read-out is affected by using the currently available RDT devices which are typically suitable for analyzing less amount of sample, such as about 5 µL of blood sample. By way of example, 100 µL of a blood sample is loaded to a channeled construct 34 of an RDT device for rapid separation of blood cells and plasma from the blood sample as an initial step. The plasma from the 100 µL blood sample comprising at least one analyte is subsequently transferred to the lateral flow unit 10 for analyte detection.

The present RDT device also avoids interference of red blood cells in sample-reading as the present RDT device is configured to exclude red blood cells from the blood sample prior to analyte detection. Thus, the detection of analyte is not affected by background noise from the presence of hemoglobin of red blood cells. The signal intensity of the RDT device improves by up to about ten times the intensity of the test by initial separation of blood cells by using a channeled construct, which is also reflected in FIGS. 8B, 11 and 14.

The RDT assay results using the RDT device are interpreted based on the presence or absence of a signal at the test region 28 on the lateral flow unit 10. The RDT assay is determined visually or by using a reader to measure the signal intensity generated at the test region 28. The reader may include a plate reader, a spectrophotometer, a fluorescence spectrophotometer, reader for measuring chemiluminescence, and the like. The present RDT device of the subject specification generates higher signal intensity compared to the commercially available benchmark devices, as shown in FIGS. 8B, 11, 13 and 14. The higher signal intensity is advantageous for detection of analytes because generally RDTs rely on visually detected changes in color of the test region 28 on a lateral flow unit 10. A faint color change is not visually detectable and could lead to a false negative result on the RDT device.

Provided herein is a channeled construct for separation of biological samples, such as blood. The channeled construct 34, as shown in FIG. 1, is configured to receive and separates one or more components of a biological sample. In case of a blood sample, the channeled construct 34 is configured to separate blood cells and plasma present in the blood sample. In some embodiments, the channeled construct comprises a size exclusion separation element. In some embodiments, the size exclusion separation element has a first surface distal from the lateral flow unit and a second surface proximal to the said lateral flow unit, when the channeled construct comprising the size exclusion separation element is vertically disposed on the lateral flow unit.

Figure 2:
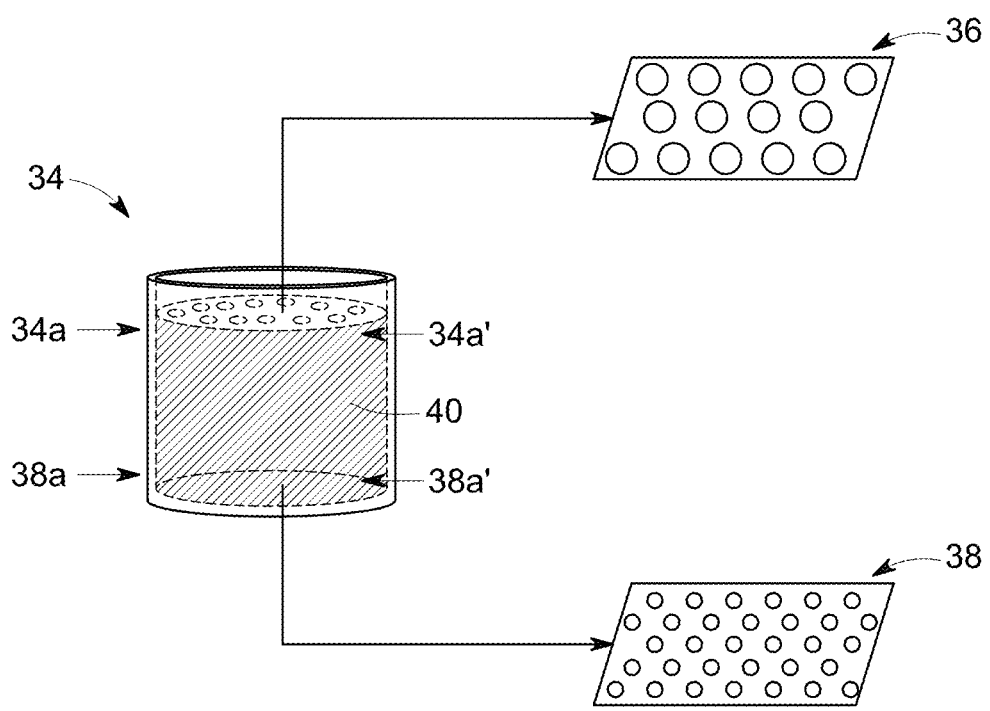
FIG. 2 is a perspective view of a channeled construct of one embodiment of an RDT device.

FIG. 2 illustrates one embodiment of the channeled construct 34 has a first surface and a second surface. The channeled construct 34 is further defined as having an upstream side 34a and a downstream side 38a. The upstream side 34a and downstream side 38a of the channeled construct 34 are defined relative to the lateral flow unit 10. The portion of the channeled construct 34 that is far from the lateral flow unit is referred to as the "upstream side" 34a, and the portion of the channeled construct 34 that is proximal to the lateral flow unit is referred to as the "downstream side" 38a.

In some embodiments, the channeled construct comprises a size exclusion separation element. In one embodiment, the first surface of the size exclusion separation element is substantially planar with a raised edge surrounding the first surface of the size exclusion separation element. At least a portion of the second surface of the size exclusion separation element is in direct contact with a first surface of the lateral flow unit that comprises the sample receiving zone, conjugate zone, and detection zone. The channeled construct allows the plasma to flow through the channels and to reach the lateral flow unit of the RDT device.

In some embodiments, the size exclusion separation element may include a membrane, a chromatographic column, chromatographic beads, or a combination thereof, for rapid separation and delivery of a biological sample. In some other embodiments, the size exclusion separation element comprises progressively narrowing channels (elongated pores), which serve to physically filter out the red blood cells from a blood sample. In some embodiments, the size exclusion separation element is a porous membrane.

The size exclusion separation element, such as a porous membrane of the channeled construct 34 ensures rapid separation of undesired materials from the biological sample to form at least partially purified biological sample comprising at least one analyte. Followed by purification, the channeled construct 34 also delivers the partially purified biological sample to the lateral flow unit 10. In some embodiments, the porous membrane employed for the channeled construct is selected from an asymmetric porous membrane, a membrane comprising affinity surfaces, a membrane comprising hydrophobic cores, or a membrane comprising charged surfaces.

In some embodiments, the channeled construct 34 comprises an asymmetric porous membrane 40 having pores with asymmetric distribution (FIG. 2). The asymmetric porous membrane 40 has a first surface and a second surface, which are referred to hereinafter as 36 and 38, respectively. The asymmetric porous membrane 40 has an upstream side 34a' and downstream side 38a'. The asymmetric porous membrane is disposed on the channeled construct such that the upstream side 34a' and downstream side 38a' of the asymmetric porous membrane are aligned with the upstream side 34a and downstream side 38a of the channeled construct 34, respectively.

The pores having larger average pore-diameter as shown in first surface 36 are on the upstream side 34a' of the asymmetric porous membrane act as a pre-filter for the separation of large particles, such as larger particles of blood sample. The pores having smaller average pore-diameter as shown in second surface 38 present on the downstream side 38a' of the asymmetric porous membrane act as an exclusion zone or cut-off layer to further filter smaller particles from the fluid, such as the red blood cells to form a plasma. For example, the said distribution of pores allows a size-based filtration whereby larger particles/cells are retained in/on the membrane, while the smaller particles/analytes flow through the membrane. Asymmetric porous membranes 40 may comprise a single layer or multiple layers. The pore size ratio of asymmetric porous membranes may vary depending on the sample being filtered.

In some embodiments, the asymmetric porous membrane 40 is manufactured using a laser cutting technique that leaves a ridge along the cut edge. In some embodiments, the asymmetric porous membrane is cut during manufacture by die cut techniques. In some embodiments, an asymmetric porous membrane is cut using knife cut techniques.

In some embodiments, the asymmetric porous membrane is a polyethersulfone membrane, a polysulfone membrane, a glass fiber, a nylon membrane, a polyester membrane, a polycarbonate membrane, a polypropylene membrane, a polyvinylidene difluoride membrane, a cellulose membrane, a nitrocellulose membrane, a cellulose acetate membrane, a nitrocellulose mixed ester membrane, a polyurethane membrane, a polyphenylene oxide membrane, a poly(tetrafluoroethylene-co-hexafluoropropylene membrane, a cellulose phosphate membrane, a cellulose/silica gel paper, a borosilicate glass membrane, a quartz membrane, or a combination thereof. In a specific embodiment, the asymmetric porous membrane is an asymmetric polysulfone membrane. In another specific embodiment, the asymmetric porous membrane is an asymmetric polyethersulfone membrane.

In some embodiments, the size exclusion separation element of the channeled construct 34 is designed as a plurality of conical shaped channels. Each of the channel has a smaller average pore diameters at the bottom of the channel 38 than the average pore diameter at the top of the channel 36. In some other embodiments, the channeled construct 34 comprises a size exclusion separation element, which is designed as a simple funnel filter for separating red blood cells. The red blood cells are unable to flow through the size exclusion separation element due to smaller pore diameter (at the bottom) than the diameter of the red blood cells. In some embodiments, each of the channels has an average pore diameter of about 10 microns to about 100 microns on the first surface 36 and an average pore diameter of about 1 micron to about 3 microns on the second surface 38 of the asymmetric porous membrane 40. In certain embodiments, the channeled construct 34 is made of a polymer, a ceramic, a glass, a metal, or a combination thereof.

In some embodiments, a first surface 36 of the asymmetric porous membrane 40 is coated with an anti-lysis coating. The first surface 36 of the asymmetric porous membrane 40 is defined as the surface where a biological sample is received in the channeled construct 34. The anti-lysis coating is used to stabilizes cells in a biological sample and prevents lysis and release of intracellular components of the cells. In some embodiments, the anti-lysis coating comprises a red blood cell stabilizer. In such embodiments, the blood separation membrane is coated with a red blood cell stabilizer that prevents lysis of the red blood cells. The prevention of cell lysis ensures minimal hemoglobin contamination during the detection step. In some embodiments, the channeled construct comprising a polymeric membrane coated with an anti-lysis coating. The polymeric membrane may be an asymmetric porous membrane.

In some alternative embodiments, the size exclusion separation element is disposed at a determined angle with respect to the lateral flow unit. In one example, the determined angle may be about 0°. In this example, the size exclusion separation element is disposed parallel to the lateral flow unit. In some of such embodiments, the parallelly disposed size exclusion separation element comprises a cellulose membrane, a nitrocellulose membrane, a glass fiber membrane, a quartz membrane, a borosilicate glass membrane, a mixed cellulose ester membrane, a polyvinylidene difluoride membrane, or a combination thereof, disposed laterally relative to the lateral flow unit. In such embodiments, the parallelly disposed size exclusion separation element allows for separation of a slower moving red blood cell front from a plasma front. Examples of such parallelly disposed membranes include but are not limited to LF1®, MF1®, VF2®, GF/DVA®, Fusion 5®, and the like.

In some embodiments, the flow of the biological sample from the channeled construct to the lateral flow unit may be pressure-driven. The pressure may be generated after closure of the housing of the device, by capillary force, by gravity, in an electric field, or by any combination thereof. Similarly, the flow may be initiated by any such method that initiates contact of the biological sample with the sample pad, test region and/or control line of the lateral flow unit including manually applied pressure.

The lateral flow unit is at least partially disposed in a cassette housing, wherein the cassette housing ensures an efficient fluidic transfer from channeled construct to the lateral flow unit with a minimal loss of the biological sample. The use of the cassette housing is advantageous especially when a large volume of a blood sample containing numerous blood cells is applied to the RDT device. The lateral flow unit and the channeled construct are disposed in the cassette housing and arranged such that the chances of sample loss are reduced significantly.

In one or more embodiments, the sample well of the cassette housing comprises at least one wall forming a channel with a top aperture and a bottom aperture, where the bottom aperture includes a flange. The bottom aperture of the cassette housing is positioned to form a gap between the bottom aperture and the channeled construct. The flange of the bottom aperture is positioned to contact the channeled construct.

The cassette housing having a first surface and a second surface, further comprises a plurality of rib structure. In some embodiments, the plurality of rib structure includes two different series of rib structure. A series of rib structure extending from the first surface of the cassette housing, referred to herein as a "first series of rib structures". The first series of rib structures are positioned adjacent to the sample well. The first series of rib structure is positioned such that a gap is formed between each of the rib structures and the sample well. The first series of rib structure is also in contact with the channeled construct.

Further, a series of rib structure extending from the second surface of the cassette housing is referred to herein as a "second series of rib structure." The second series of rib structure extending from the second surface of the cassette housing are positioned on the second surface to form a gap between the rib structures and the channeled construct. The second series of rib structure is positioned such that a gap is formed between the rib structures and the lateral-flow unit.

In an alternative embodiment, the cassette housing is opened and a channeled construct is placed adjacent to the lateral flow unit such that one edge (proximal end) of the channeled construct contacts the lateral flow unit. The other edge of the channeled construct (distal end) placed adjacent to the sample well for receiving the biological sample. For example, the channeled construct employed for these embodiments may be L-shaped. The sample is received on the distal end of the L, wherein the heavier red blood cells are retained in the channeled construct while the plasma of the blood sample reaches the sample receiving zone of the lateral flow unit.

Figure 3:
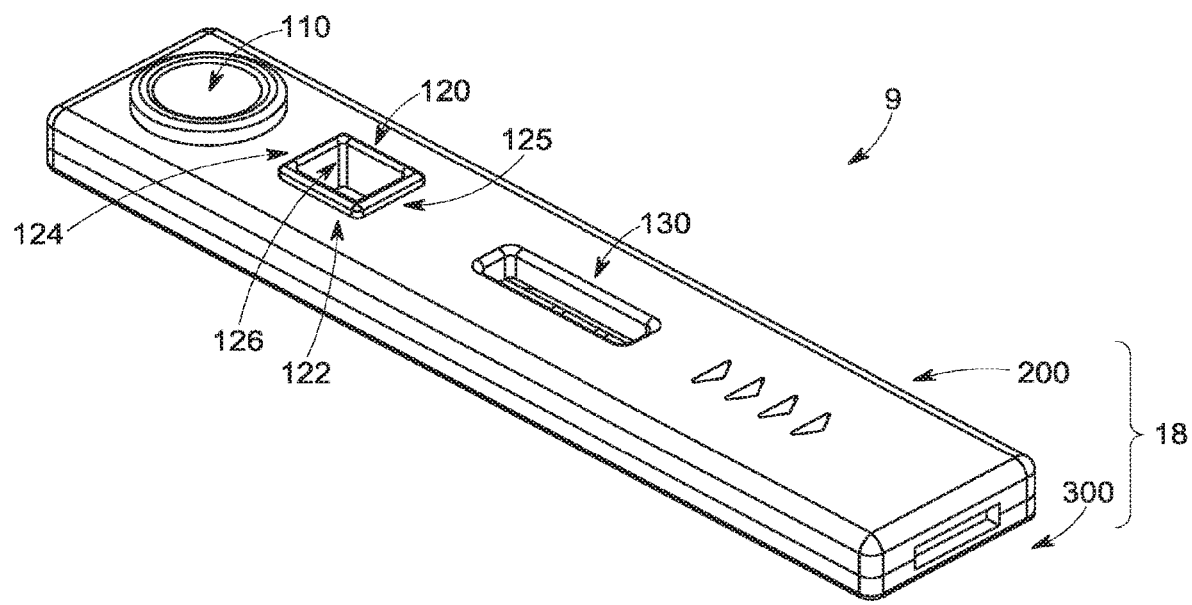
FIG. 3 is a perspective view of one embodiment of an RDT device for rapid diagnostic testing of biological samples.

FIGS. 3-7 illustrate different views of an RDT device 9 of the present specification. In particular, FIG. 3 illustrates an embodiment of an RDT device 9 for rapid diagnostic testing of biological samples. In one embodiment, the RDT device includes a cassette housing 18, which is made of a top section 200 and a bottom section 300. Other embodiments do not include a top section and a bottom section of the cassette housing, for example an integrally whole cassette housing or a cassette housing fabricated from more than two sections.

As noted, the cassette housing 18 has a first surface and a second surface, wherein the first surface is an outer surface of the top section 200 and the second surface is an outer surface of the bottom section 300 of the cassette housing 18. In the embodiment illustrated in FIG. 3, the cassette housing 18 includes a buffer well 110 disposed within the cassette housing 18. The buffer well 110 is of a size, shape and position to permit receiving buffer to the RDT device 9 during analyte detection process. The lateral flow unit 10 is disposed in the cassette housing 18 such that the buffer well 110 is disposed adjacent to the buffer reservoir 20 of the lateral flow unit 10. The buffer well 110 is configured to flow buffer onto the buffer reservoir 20 of the lateral flow unit 10. The cassette housing 18 includes a test window 130. The test window 130 includes an aperture positioned adjacent to the test region 28 of the detection zone 26 of the lateral flow unit 10. The buffer well 110 is positioned adjacent to an end of the cassette housing 18 and the test window 130 is positioned centrally, adjacent to the sample well 120 of the cassette housing 18.

The cassette housing 18 also includes a sample well 120. In the embodiment shown in FIG. 3, the sample well 120 is positioned between the buffer well 110 and the test window 130. The sample well 120 is of a size, shape and position to permit a biological sample to traverse through the sample well 120 and to be deposited on to a channeled construct 34 positioned within the cassette housing 18. In some embodiments, the sample well 120 includes at least one wall 126 forming a channel with a top aperture 124 and a bottom edge/aperture 122. The sample well 120 includes a bottom edge adjacent to a first surface 36 of the channeled construct 34. The bottom edge 122 of the sample well 120 includes a flange 125 that contacts the first surface 36 of the channeled construct 34 disposed in the cassette housing 18.

The bottom edge 122 of the sample well 120 is positioned such that there is a gap between the bottom edge of the sample well 120 and the first surface 36 of the channeled construct 34. The flange 125 may be positioned to direct the flow of a biological sample from the sample well 120 onto the first surface 36 of the channeled construct 34. The gap between the bottom edge 122 of the sample well and the first surface 36 of the channeled construct 34 may vary based on several factors that can influence the speed and performance of the diagnostic test. By way of example, the gap may be varied based on factors such as the biological sample to be assayed using the RDT device, a flow rate of the intended biological sample through the channeled construct, and a reaction rate of the binding assay within the lateral flow unit.

In some embodiments, a channeled construct 34 is of a size and shape to form a gap between an edge of the channeled construct 34 and an interior wall of the cassette housing 18. In some embodiments, the cassette housing 18 may be of a size, shape and position to secure the second surface 38 of the channeled construct 34 against the first surface of the lateral flow unit 10. The entire second surface 38 of the channeled construct 34 need not, depending on the embodiment, be in contact with the first surface of the lateral flow unit 10.

Figure 4:
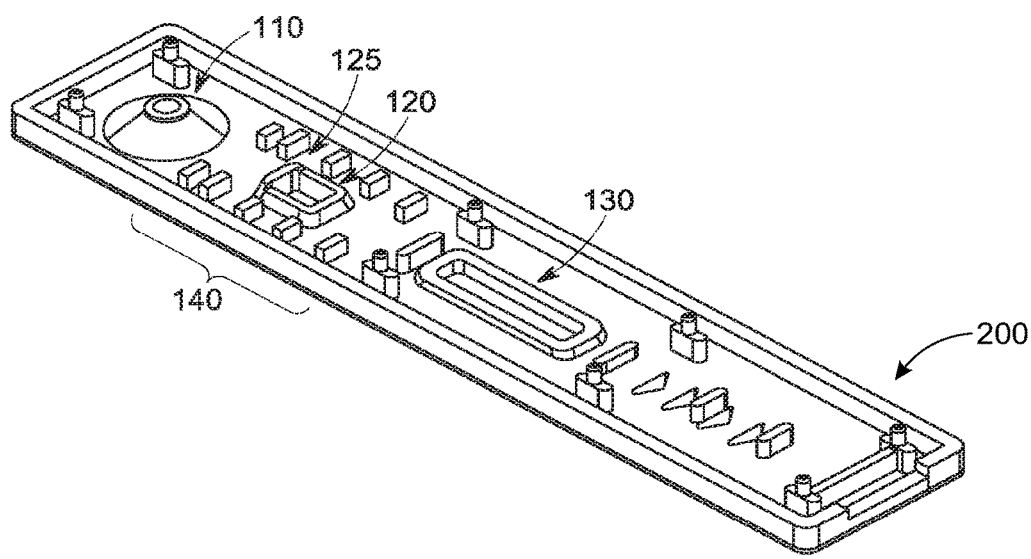
FIG. 4 is a perspective view depicts an interior of a first section of a cassette housing of one embodiment of an RDT device.

FIG. 4 illustrates an insider view of the top portion 200 of the cassette housing 18 of FIG. 3. In some embodiments, a cassette housing may be fabricated as three sections, or four sections, and then assembled into a complete cassette housing during manufacture of the RDT device. The top portion 200 of the cassette housing 18 includes a buffer well 110, wherein the buffer well 110 is shaped as a frustum, with a wide portion oriented towards the top of the cassette housing and a narrow portion oriented towards the interior of the cassette housing 200. A flange 125 is affixed to an edge of the sample well 120, the flange projecting into the interior of the cassette housing 200. When the top section of the cassette housing 200 is in position for use, the flange 125 is positioned substantially vertically within the cassette housing 200 such that the lower edge of a flange 125 contacts the first surface of the channeled construct 34.

Figure 5:
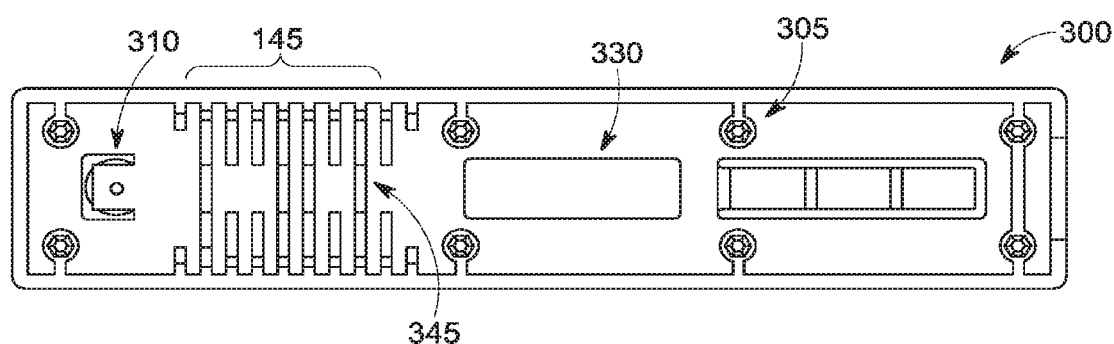
FIG. 5 is a perspective view depicts an interior of a second section of a cassette housing of one embodiment of an RDT device.

In some embodiments, the plurality of rib structure is formed as non-rectangular shapes, for example as ovoid shapes. In some embodiments, the plurality of rib structures includes: first series of rib structure 140 and a second series of rib structure 145. The two series, first series and second series of rib structure can be numbered, shaped and positioned differently from each other. For example, the first series of rib structure 140 extending from the first surface of the cassette housing (FIG. 4). The second series of rib structure 145 extending from the second surface of the cassette housing need not be mirror images of each other (FIG. 5). In some embodiments, the first series of rib structure 140 is positioned adjacent to the sample well 120 such that it forms a gap between each of the rib structure and the sample well 120. Further, the first series of rib structure 140 is positioned such that the rib structure 140a contacts a top side of the channeled construct 34 and the rib structure 140b contacts a top surface of the lateral flow unit 10. In some other embodiments, the channeled construct may be of a size, shape and position to form a gap between an edge of the channeled construct 34 and the first series of rib structure 140 of the cassette housing 18. In some embodiments, the second series of rib structure 145 is positioned to form a gap between the rib structure and the channeled construct 34. Further, the second series of rib structure 145 is positioned such that a gap is formed between the rib structure 145 and at least one lateral flow unit 10. The plurality of rib structure 140 affixed to the interior of the top section of the cassette housing 200, as shown in FIG. 4. The rib structure is substantially rectangular in shapes, with a long axis of the rectangle positioned substantially perpendicular to the long axis of the top section of the cassette housing 200.

FIG. 5 depicts an insider view of a bottom section 300 of the cassette housing 18 of FIG. 3. For example, a bottom section of the cassette housing 300 may be used in combination with a top section of the cassette housing 200 to form a whole cassette housing 18 to manufacture an RDT device 9. A plurality of fastening regions 305 are positioned around the periphery of the bottom section of the cassette housing 300. The bottom section of the cassette housing 300 includes an attachment region 310. The attachment region 310 is of a size and shape to secure an end of a lateral flow unit 10 in position within the RDT device 90. In some embodiments, an attachment region 310 is positioned to be adjacent to a buffer well 110 of the RDT device. The bottom section of the cassette housing 300 also includes an elevated section 330. The elevated section 330 is positioned so that it is adjacent to the test window of the RDT device. The elevated section 330 can, for example, be of a size, shape and position to hold a lateral flow assay unit adjacent to the test window 130 for visualization or use with an assay reader device.

Depending on the embodiment, a cassette housing 18 can be fabricated from materials selected for features such as weight, cost, durability, and chemical interactions with the interior features of the device. For example, in some embodiments the cassette housing is fabricated from a plastic material. For example, in some embodiments, the cassette housing is fabricated by a hydrophobic material. For example, in some embodiments the cassette housing is fabricated from a hydrophobic plastic material.

The bottom section of the cassette housing 300 illustrated in FIG. 5 includes a series of rib structure 145. The rib structure 145 includes a series of steps or notch shapes on the distal edges of the series of rib structure 145. The series of rib structure affixed to the bottom portion of the cassette housing can be, for example, of a size, shape and position to support a channeled construct 34 to be disposed within the cassette housing. The series of rib structures need not be simple rectangular shapes; in some embodiments, they are shaped with steps, notches, and/or grooves. The series of rib structure can, for example, be of a size, shape and position to form a gap between a surface of the channeled construct 34 and one or more of the surfaces of the facing edges of the series of rib structure 145. In some embodiments, the gap between the first surface 36 of the channeled construct 34 and one or more of the surfaces of the facing edges of the series of rib structure is at least 500 microns. In some embodiments, a series of rib structures 145 includes an indentation 345 running though the approximate center of the series of rib structures 145. The indentation 345 can be of a size and shape to hold a lateral flow strip such that the top surface of the lateral flow unit 10 (assay strip) is above the top edge of the series of rib structures 145. The indentation 345 can be of a size and shape to hold a lateral flow unit 10 such that there is a gap between the outer edges of the lateral flow unit 10 and the facing surfaces of the series of rib structures.

Figure 6:
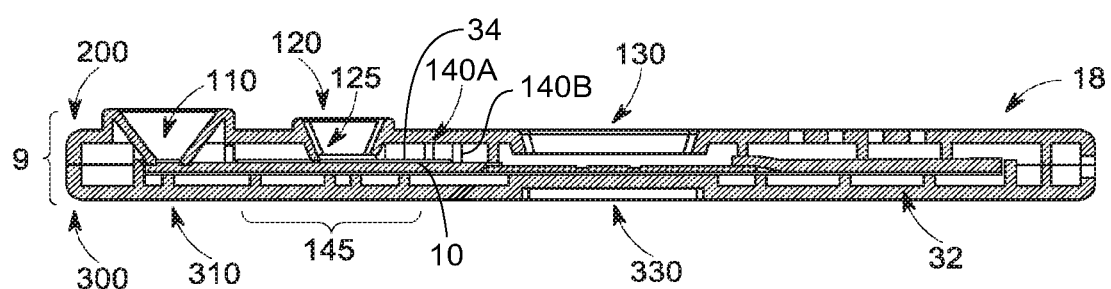
FIG. 6 is a perspective view of a vertical cross section of one embodiment of an RDT device.

FIG. 6 depicts a vertical cross section of the RDT device 9 of FIG. 3 for rapid diagnostic testing of biological samples. An attachment region 310 is positioned adjacent to the lower edge of the buffer well 110. A lateral flow unit 10 is positioned beneath the aperture formed by the buffer well and one end of the lateral flow unit 10 is positioned within the attachment region 310. The second series of rib structures 145 are also of a size, shape and position to create a gap between the outer edge of the lateral flow unit 10 and the adjacent facing surfaces of the series of rib structure 145. Similarly, the series of rib structure 145 is also of a size, shape and position to create a gap between a surface of the channeled construct 34 and the adjacent facing surfaces of the series of rib structures 145. The RDT device 9 includes a raised area 330, which is positioned adjacent to a lower edge of the test window 130. The raised area 330 is of a size, shape and position to hold the lateral flow strip 10 in a location for visualization through the test window 130. The lateral flow strip 10 contacts a wicking pad 32 at the end of the lateral flow strip 10 distal to the buffer well 110.

Figure 7:
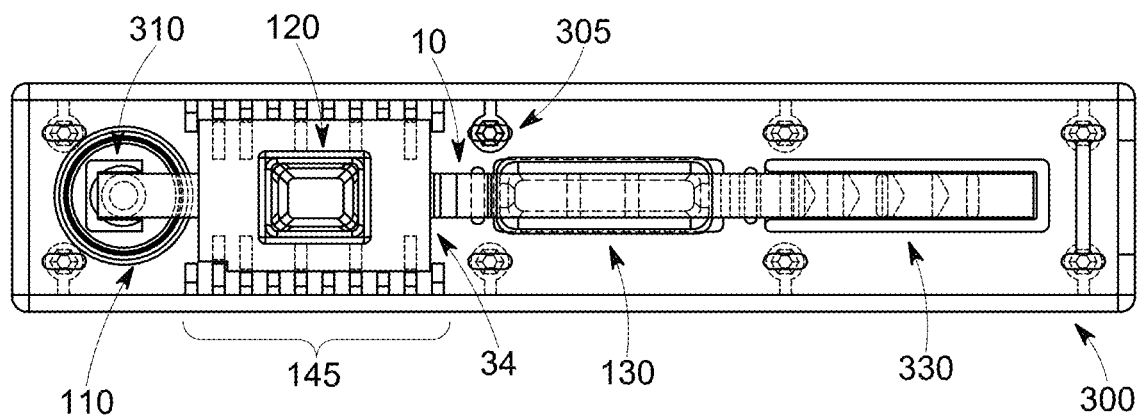
FIG. 7 illustrates a top view of one embodiment of an RDT device including the channeled construct, lateral flow unit and a second section (at the bottom) of a cassette housing.

FIG. 7 illustrates a top down view of an embodiment of an RDT device 9 for rapid diagnostic testing of biological samples. The top down view of the RDT device illustrates the interior of the device. A group of fastening regions 305 positioned on the bottom cassette housing 300 can be utilized to affix a top section of the cassette housing relative to the bottom section of the cassette housing 300 in a manufactured device. The first end 12 of the lateral flow unit 10 is held in position relative to the cassette housing at the attachment region 310. The device includes a sample well 120, which could be included in a top cassette housing. The sample well 120 is positioned above a channeled construct 34. The channeled construct 34 is maintained in position relative to the cassette housing with a series of rib structure 145. In the illustrated embodiment, the series of rib structure 145 is asymmetrical relative to the long midline of the bottom cassette housing 300. An asymmetrical configuration can, for example, be helpful during manufacturing to ensure proper orientation of a channeled construct 34. The lateral flow unit 10 is positioned relative to the test window 130 so that the test region 28 of the lateral flow unit 10 may be visualized by a user of the assay. The second end 14 of the lateral flow unit 10 contacts a wicking pad 32.

The rapid diagnostic testing devices described herein are applicable to a variety of RDTs including RDTs for detection of viruses, infectious diseases, bacteria, cancers, cardiac problems, animal diseases, sexually transmitted diseases, forensics, and the like.

The rapid diagnostic testing devices described herein may also be further adapted by including additional components such as colorimetric readers, photothermal readers, fluorescence readers, chemiluminescence readers, magnetic readers and the like. While typical RDTs are immune-chromatographic assays which rely on antibody conjugates, dye labeled antibodies, or sandwich assays for detection, other methods of detection are contemplated within the scope of embodiments described herein including and not limited to colorimetric particles (metal particles, polymeric beads labeled with dyes, etc.), fluorescence, chemiluminescence, magnetic beads and the like. In addition to antibody capture, the analyte may be captured by techniques such as nucleotide/aptamer binding and such variants are contemplated as being within the scope of embodiments presented herein. It will be recognized that there are many types of assays such as competitive and non-competitive assays and such variations are also contemplated as being within the scope of embodiments presented herein. Further, multiple detection strips, and/or strips with multiple detection lines may be employed in the devices and methods described herein.

In some embodiments, the analyte is an antigen. In some embodiments, the analyte is selected from a malarial biomarker, an influenza biomarker, cardiac biomarker, a tumor biomarker, or a combination thereof. In some other embodiments, the analyte is a cardiac biomarker CK-MB. In certain embodiments, the analyte is a malarial biomarker present in the blood sample. The analyte is a malarial biomarker HRP2 (histidine rich protein II) present in the blood sample. HRP2 is one of the five malaria proteins (HRP1, HRP2, EMP1, EMP2, and EMP3), which are on typically the surface or in association with the cytoskeleton of erythrocytes infected with *Plasmodium falciparum*. HRP2 is a histidine- and alanine-rich protein, which is being produced and secreted by the parasite during its growth and development.

EXAMPLES

Example 1

Effect of a Conjugate Zone (Conjugate Pad) Location

Figure 8A:
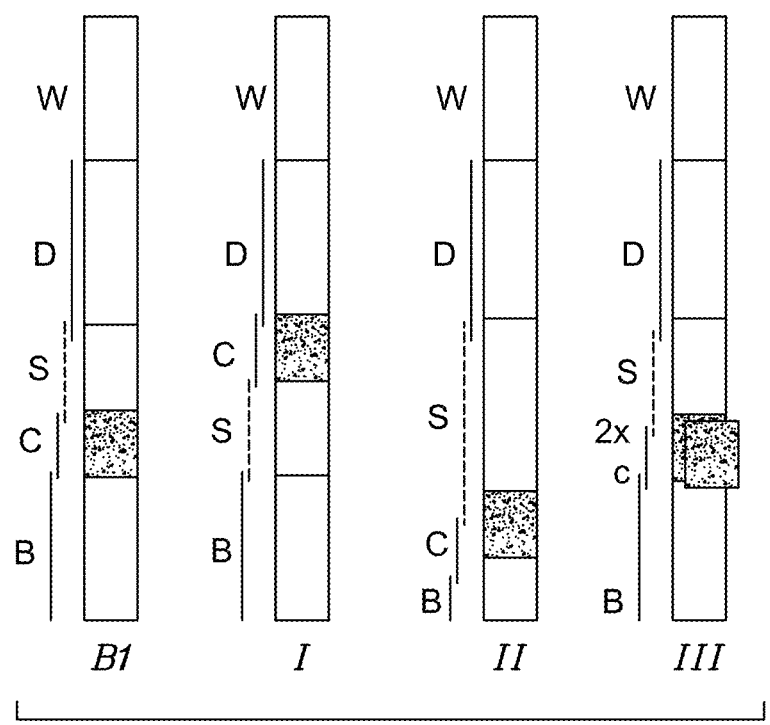
FIG. 8A illustrates different configurations of the lateral flow unit used for one embodiment of an RDT device.

RDT device constructs: The different RDT device constructs were made for testing the detection assay performance which are shown in FIG. 8A. In a benchmark device, the conjugate zone and detection zone were separated by a sample receiving zone, which was used herein as a control and is referred to herein as "Benchmark 1" (or B1 as shown in FIG. 8A). The conjugate zone of a Benchmark 1 was moved up to be adjacent to detection zone forming device construct I, or moved down such that it was further away from detection zone forming device construct II, or an additional conjugate pad (2x) was added to its original location and formed device construct III. A channeled construct was placed on top of the conjugate/sample receiving zone, and the housing was closed until testing. Different zones, such as buffer reservoir, sample receiving zone, conjugate zone, detection zone and wicking pad on the lateral flow unit are represented by B, S, C, D and W, respectively, in different device constructs of FIG. 8A.

Testing procedure: (1). HRP2 (CTK A3005) dilutions in citrate phosphate dextrose (CPD) human whole blood (BioReclamation) was prepared; (2) The housing was open, added 75 µl blood sample slowly onto center point of the channeled construct. (3) The housing was closed, and chased the blood sample with 100 µl non-lytic buffer through buffer reservoir—(Buffer I: Borate, 0.5% BSA, 0.5% Tween 20, pH 9, and Buffer II: PBS, 0.5% BSA, 0.5% Tween 20, pH 7.4). Buffer I was used for devices with conjugate pads of type I and Buffer II was used for devices containing conjugate pads other than type I). (4) Covered RDT to minimize evaporation from detection window. (5) 5 µl blood was run in RDTs as control by following manufacturer instructions. The results obtained after 30 minutes, quantified with image J.

Figure 8B:
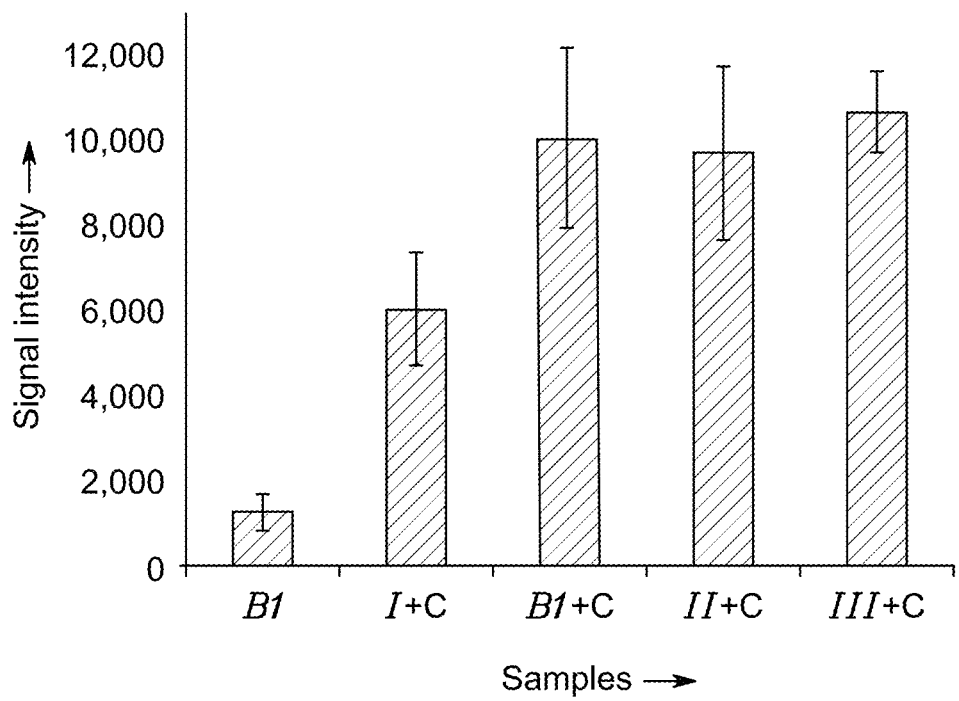
FIG. 8B shows bar graphs illustrating fluorescence signal intensity of the test line of one embodiment of an RDT device using different configurations of the lateral flow units as shown in FIG. 8A in presence and absence of a channeled construct.

Result: The test was performed with 5 µl blood sample at the concentration of 10 ng/ml HRP2 level using the Benchmark 1 as a control, which was without a channeled construct. As shown in FIG. 8B, an average signal intensity of 1255 was generated using the control (Benchmark 1 or B1), which was improved by nearly 10-fold when the channeled construct was present along with the control device (Benchmark 1+C or B1+C). In the control device with channeled construct (Benchmark 1+C) was configured to receive 75 µl blood. When the conjugate pad was moved closer to the detection zone (device construct I+C), loss of signal intensity was observed. This was due to mismatched delivery rate of conjugate particles and analyte onto the test line of the detection membrane, wherein most of the particles passed the test line before reacting with the analyte. Moving conjugate pad further away from detection zone (device construct II+C), or adding an extra conjugate pad (device construct III+C) to the control device structure with channeled construct (Benchmark 1+C) had no effect on the final signal intensities. The signal intensity was increased when the distance between the conjugate zone and the detection zone was increased. Though onset of signal was affected, the longer the distance between the conjugate zone and the detection zone, the slower the signal onset. Therefore, when dealing with large sample volume, it is critical to ensure thorough mixing of conjugate particles with analyte before they pass the test line.

Example 2

Effect of Particle Type in Benchmark 1 Configuration

Figure 9:
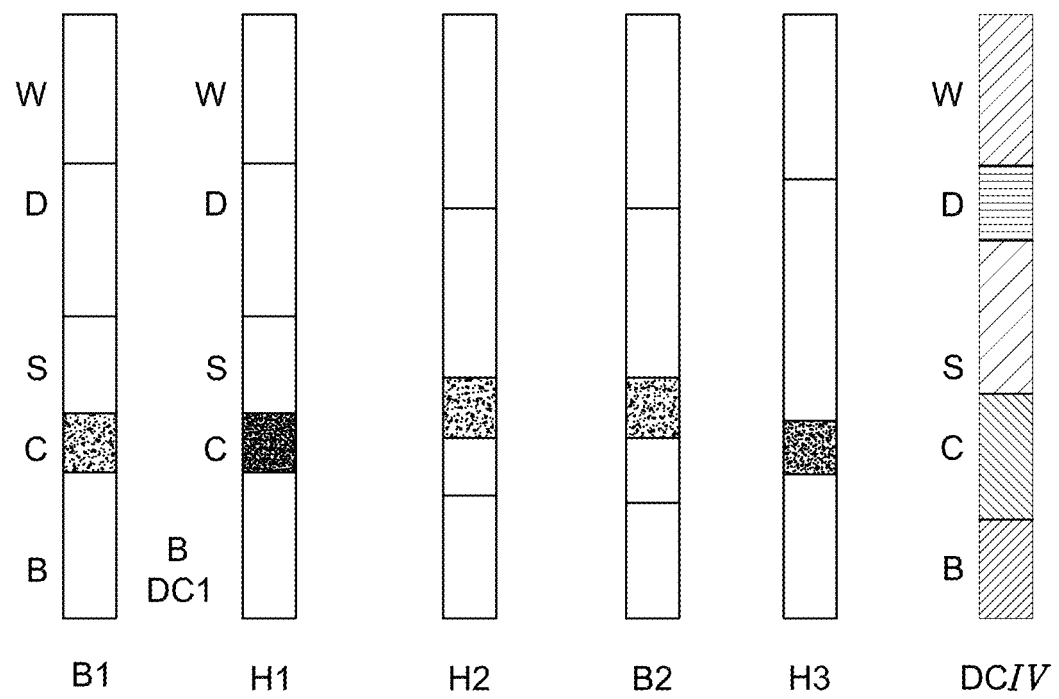
FIG. 9 depicts different configurations of the lateral flow units of one embodiment of an RDT device.

HRP2 was tested using other available benchmark products (Benchmark 1 or B1, Benchmark 2 or B2) and a product developed in the laboratory ("device construct V") using cellulose nanobeads as the conjugate particles. The devices construct V and Benchmark 2 were different than the Benchmark 1 in their configurations. The conjugate zones of the Benchmark 2 device and device construct IV were adjacent to the detection zones, which did not allow complete mixing of analytes and conjugate particles before the conjugate particles reached the test lines. This led to less performance improvement even if a channeled construct was added. Different device constructs, such as Hybrid 1 (H1), Hybrid 2 (H2), and Hybrid 3 (H3) were made by using a conjugate pad, a detection pad or a sample receiving pad from different device constructs, such as, Benchmark 1, Benchmark 2 and device construct IV. Hybrid 1 was made by replacing the conjugate pad of the Benchmark 1 with the conjugate pad of Benchmark 2. Hybrid 2 was made by replacing the conjugate pad and detection pad of the Benchmark 1 with the conjugate pad and detection pad of Benchmark 2. Hybrid 3 was made by replacing the conjugate pad of the Benchmark 1 with the conjugate pad of device construct IV (DC IV) as shown in FIG. 9. The performance improvements by adding a channeled construct to those device constructs with replaced conjugate pads (hybrid 1, hybrid 2, hybrid 3) were then investigated. For comparison, improvements by adding a channeled construct for these conjugate pads in their original device configurations were also evaluated.

Testing procedure: (1) HRP2 (CTK A3005) dilutions in citrate phosphate dextrose (CPD) human whole blood (BioReclamation) was prepared. (2) The housing was open, added 75 µl blood sample slowly onto center point of the channeled construct. (3) The housing was closed and the blood sample was chased with 100 µl non-lytic buffer through buffer reservoir (Buffer I: Borate, 0.5% BSA, 0.5% Tween 20, pH 9, and Buffer II: PBS, 0.5% BSA, 0.5% Tween 20, pH 7.4); Buffer I was used for devices with conjugate pads of type I and Buffer II was used for devices containing conjugate pads other than type I. (4) RDT was covered to minimize evaporation from detection window. (5) 5 µl blood was run in RDTs as control by following manufacturer instructions. (6) The results obtained after 30 minutes, quantified with image J.

Figure 10:
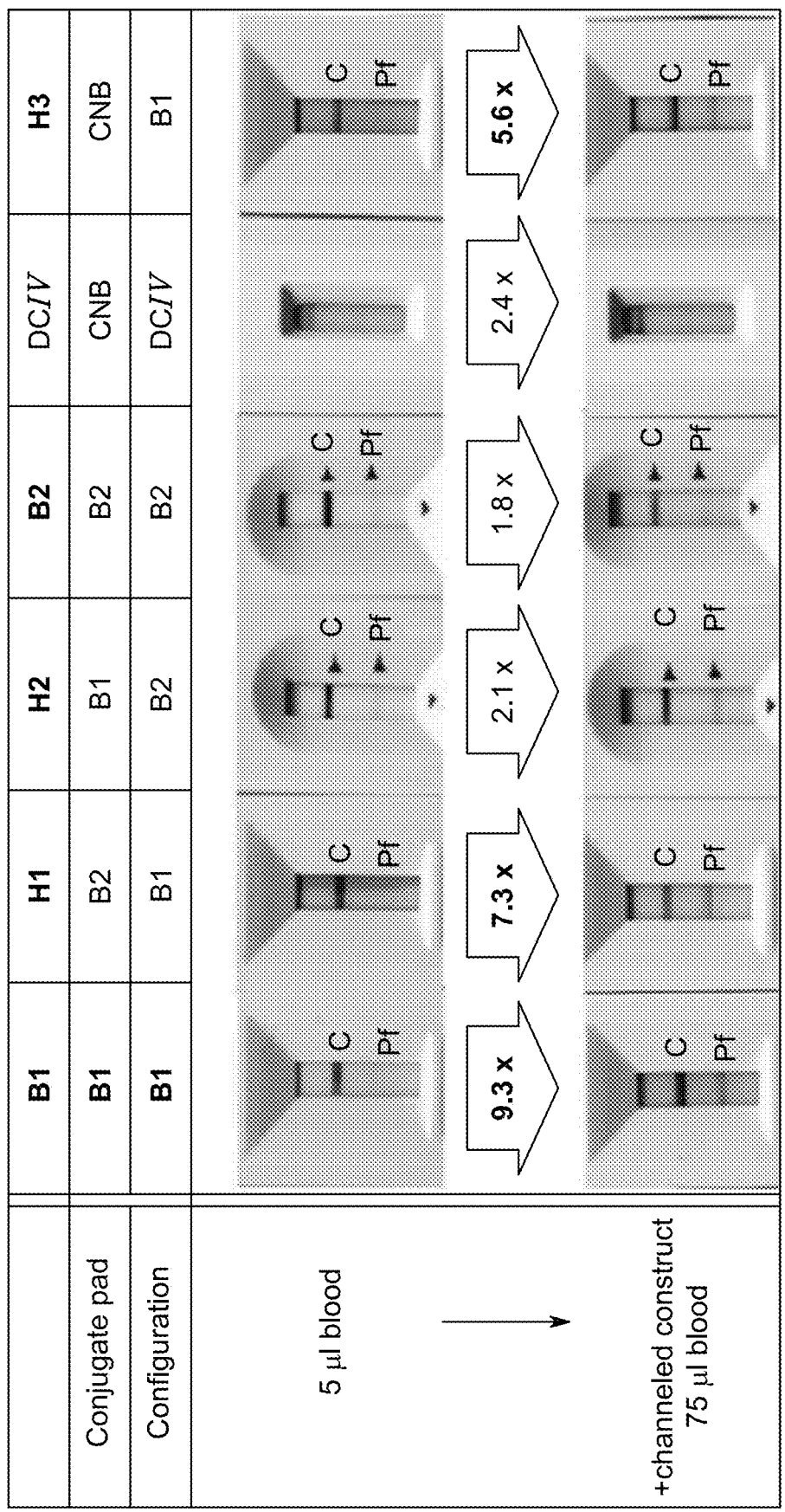
FIG. 10 illustrates variation in signal intensities for test lines and control lines using different configurations of the lateral flow units as shown in FIG. 9, in presence and absence of channeled constructs.

Results: The test results with 10 ng/ml blood sample were shown in FIG. 10. Generally, in the device configurations (B2) where conjugate zone was right on the detection membrane, about 2× improvement was observed by adding a channeled construct, regardless of particle type as shown in FIG. 10, columns 3 and 4. In the Benchmark 1 (B1), where the conjugate zone was separated from detection zone by a sample receiving zone, much higher (about 10×) improvement was observed by addition of a channeled construct (FIG. 10, column 1). Differences between the particle type used were also observed (FIG. 10, column 2, and 6), however that could be due to the inherent differences in rehydration speed for the different conjugate pads used. The mixing efficiency of particles and analytes may be affected by the rehydration speed for the different conjugate pads. Device configuration DC IV with CNB coated conjugate pad (column 5, FIG. 10) showed around 2× improvement on addition of a channeled construct. The lateral flow units (B1) configured to receive 5 µl blood sample are shown in upper panel and the lateral flow units with channeled construct (B1+C) configured to receive 75 µl blood sample are shown in lower panel. The device B1 and B1+C showed two lines at the test window, one is for control (C) and another is for HRP2 analyte at the test region as Pf (*Plasmodium falciparum*).

Example 3

Figure 11:
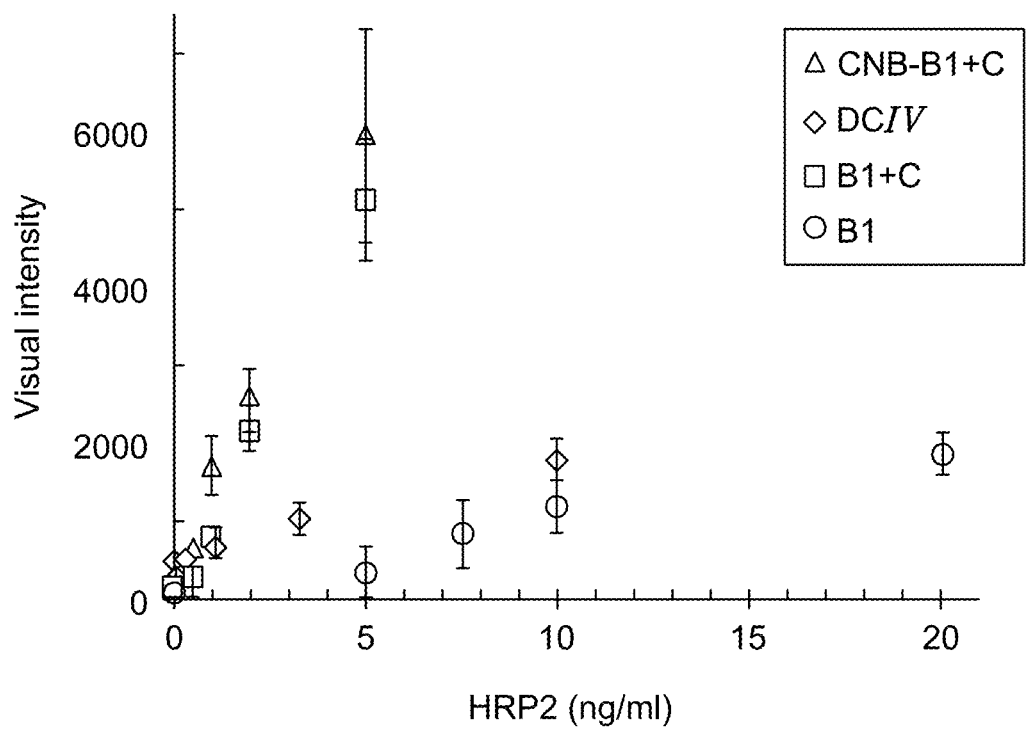
FIG. 11 illustrates performance characteristics of different embodiments of RDT device showing detection limits of channeled construct using malarial biomarker HRP2.

Detection of Analyte HRP2 and Quantification of Sensitivity at Low HRP2 Concentration In configuration of Benchmark 1, the performances of channeled constructs were tested in broader concentration range to estimate the improvement on limit of detections, for both cellulose nanobeads (CNB) of device construct IV and conjugate particles of Benchmark 1. The quantified results were shown in FIG. 11. For either particle type, there are nearly 10× improvements in both signal intensities and estimated lower detection limits (FIG. 11).

A configuration of the RDT device (as shown in FIG. 1) having a sample receiving zone between conjugate zone and detection zone ensured thorough mixing of particles and analytes before the particles pass the test line. In another example, the conjugate zone and the sample receiving zone were also disposed on a single pad, when the conjugate particles were sprayed at one end of the pad, leaving enough distance between conjugate zone and detection zone for mixing purpose (data not shown).

Example 4

Detection of Analyte CK-MB and Quantification of Sensitivity at Low CK-MB Concentration Creatine Kinase-MB (CK-MB) was tested using benchmark product (Benchmark 1 or B1) and a benchmark product in presence of channeled construct (B1+C).

Testing procedure: (1) CK-MB (Bio Rad) dilutions in citrate phosphate dextrose (CPD) human whole blood (Bio Reclamation) was prepared. (2) The housing was open, added 150 µl blood sample slowly onto the center point of the channeled construct of B1+C configuration of the RDT device. (3) The housing was closed, and the blood sample was chased with 100 µl non-lytic buffer through buffer reservoir (Buffer I: Borate, 0.5% BSA, 0.5% Tween 20, pH 9, and Buffer II: PBS, 0.5% BSA, 0.5% Tween 20, pH 7.4); Buffer I was used for devices with conjugate pads of type I and Buffer II was used for devices containing conjugate pads other than type I). (4) The RDT was covered to minimize evaporation from detection window. (5) 60 µl blood was run in B1 configuration of the RDT device as control by following manufacturer instructions. (6) The results obtained after 30 minutes, quantified with image J.

Figure 12A:
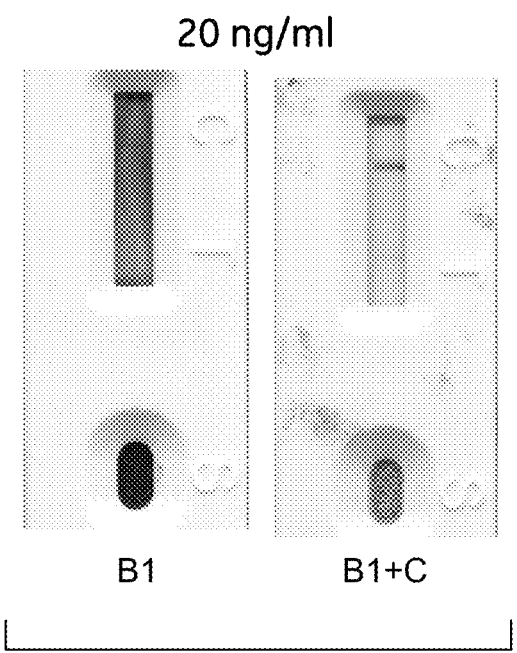
FIG. 12A illustrates variation in signal intensities for test lines and control lines using one embodiment of an RDT device, in presence (B1+C) and absence (B1) of channeled constructs. using cardiac biomarker CK-MB (20 ng/ml).
Figure 12B:
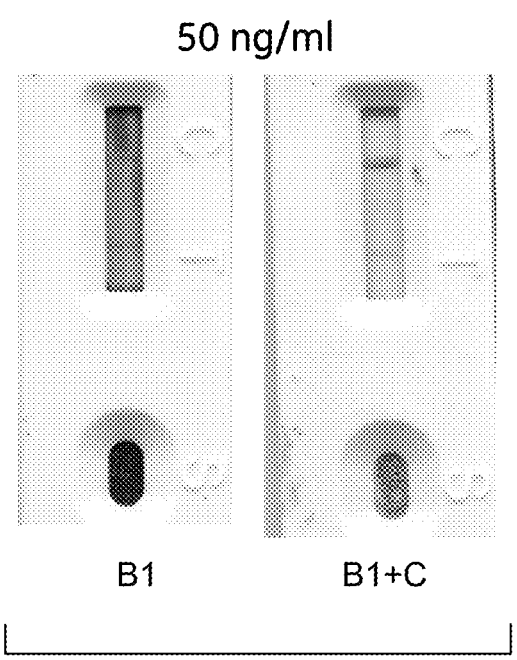
FIG. 12B illustrates variation in signal intensities for test lines and control lines for detection of cardiac biomarker creatine kinase-MB (CK-MB) (50 ng/ml) using one embodiment of an RDT device, in presence (B1+C) and absence (B1) of channeled constructs.

Results: The test results with 20 ng/ml blood sample were shown in FIG. 12A and 50 ng/ml blood sample were shown in FIG. 12B. In the Benchmark 1 (B1), where the conjugate zone was separated from detection zone by a sample receiving zone, much higher (about 10×) improvement was observed by addition of a channeled construct (FIGS. 12A and 12B, B1+C). The mixing efficiency of particles and analytes may be affected by the rehydration speed for the different conjugate pads.

Figure 13:
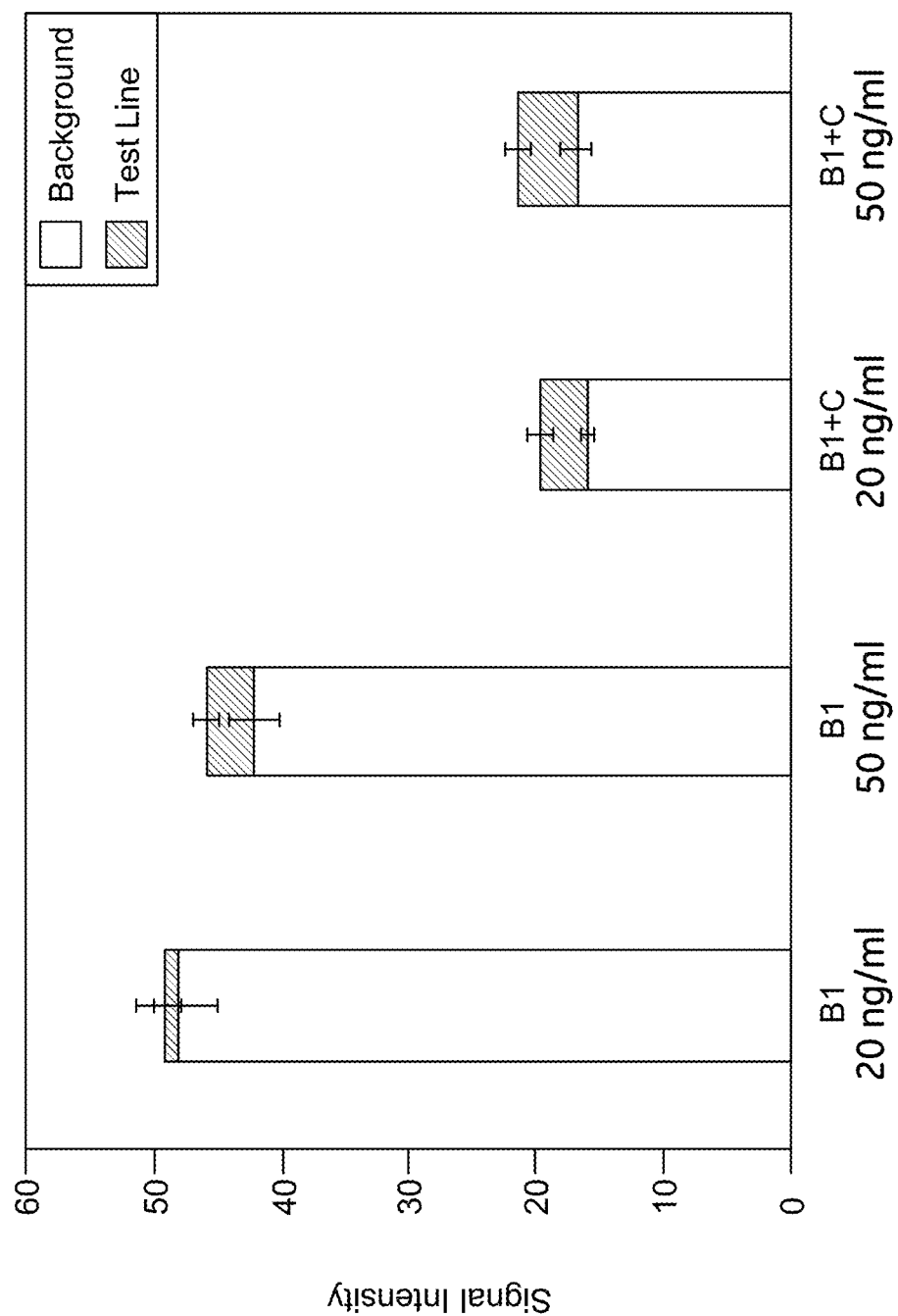
FIG. 13 shows bar graphs illustrating background signal intensity and test line signal intensity for detection of cardiac biomarker creatine kinase-MB (CK-MB) (50 ng/ml, 20 ng/ml) using one embodiment of an RDT device, in presence (B1+C) and absence (B1) of a channeled construct.
Figure 14:
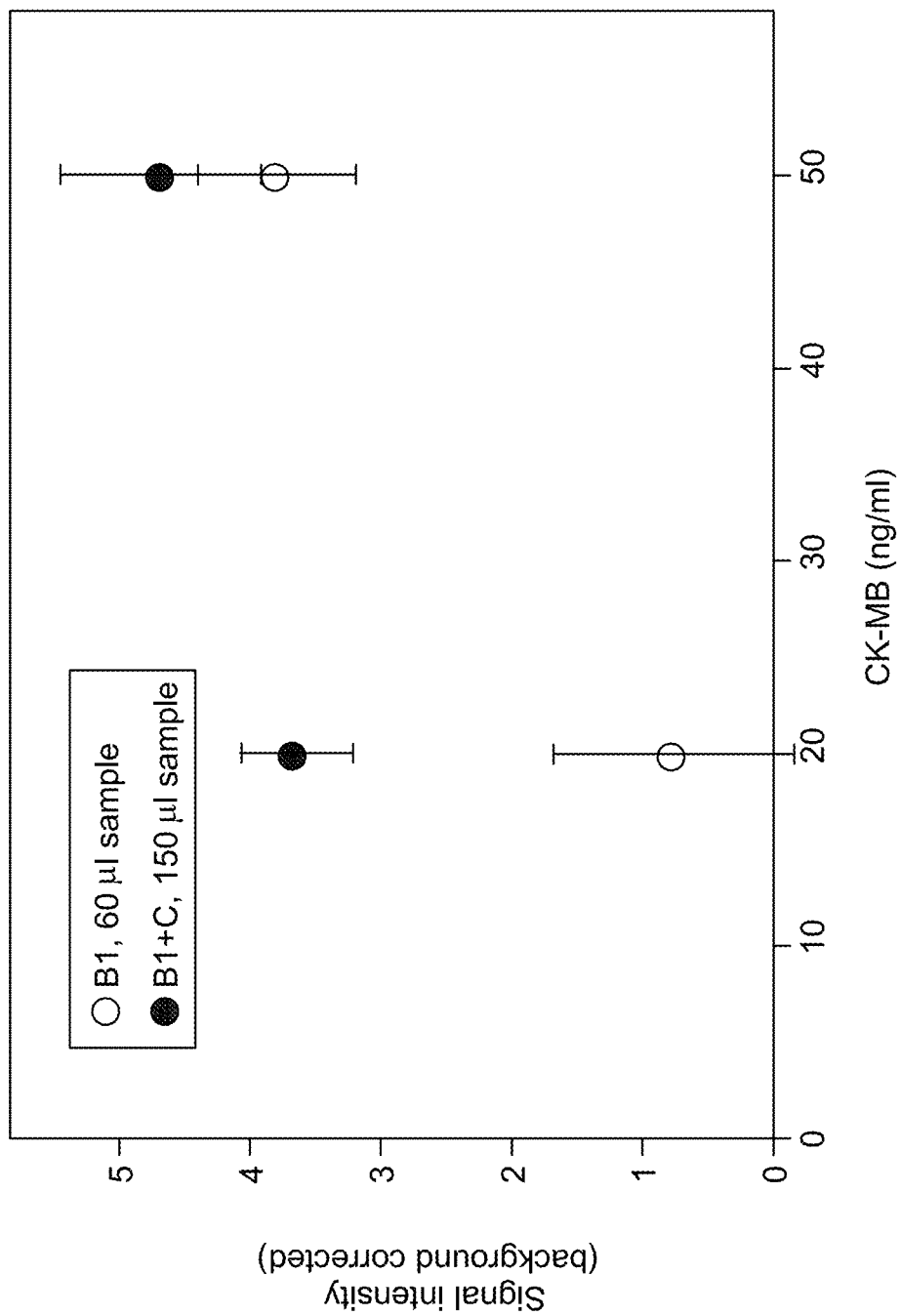
FIG. 14 is a graphical representation of performance characteristics of one embodiment of an RDT device, in presence (B1+C) and absence (B1) of a channeled construct, for detection assay of cardiac biomarker CK-MB.

In configuration of Benchmark 1, the performances of channeled constructs were tested in broader concentration range to estimate the improvement on limit of detections for B1 and B1+C using 20 ng/ml blood sample and 50 ng/ml blood sample. The quantified results were shown in FIGS. 13 and 14. FIG. 13 showed significant decrease of background signal and improved signal to noise ratio for device construct B1+C compared to B1. For either concentration, there are nearly 3× improvements in both signal intensities and estimated lower detection limits using channeled construct as shown in FIG. 14.

While only certain features of the invention have been illustrated and described herein, many modifications and changes will occur to those skilled in the art. It is, therefore, to be understood that the appended embodiments are intended to cover all such modifications and changes as fall within the scope of the invention.

The invention claimed is:
1. A rapid diagnostic testing device for rapid diagnostic testing of a biological sample, comprising:
   a channeled construct comprising a first surface and a second surface, wherein the first surface is configured to receive at least a portion of the biological sample and wherein channels of the channeled construct narrow from the first surface to the second surface such that the portion of the biological sample passes through the channels at the second surface to form at least partially purified biological sample;
   at least one lateral flow unit operatively coupled to the channeled construct at the second surface, wherein the lateral flow unit comprises:
      a sample receiving zone operatively coupled to the channeled construct for receiving the partially purified biological sample from the channeled construct, wherein the partially purified biological sample comprises at least one analyte, and wherein the sample receiving zone comprises a first side and a second side;
      a conjugate zone disposed adjacent to the first side of the sample receiving zone, wherein the conjugate zone comprises a conjugate particle for binding with the analyte; and a detection zone disposed adjacent to the second side of the sample receiving zone, wherein the detection zone comprises at least one binding agent for detecting the analyte by capturing the analyte; and a cassette housing comprising a sample well and a plurality of rib structures extending from the cassette housing into an interior space formed by the cassette housing and proximate to the sample well such that a first rib structure of a first series of the plurality of rib structures extends from a top section of the cassette housing into the interior space a smaller distance relative to a second rib structure of the first series of the plurality of rib structures, wherein the first rib structure is closer to the sample well than the second rib structure, wherein the lateral flow unit is at least partially disposed in the interior space of the cassette housing, wherein a second series of the plurality of rib structures extends from a bottom section of the cassette housing, wherein the first rib structure contacts the first surface of the channeled construct, wherein the first surface is a top side of the channeled construct, and wherein the second rib structure contacts a top surface of the lateral flow unit.

2. The rapid diagnostic testing device of claim 1, wherein the biological sample comprises blood, feces, sweat, saliva, mucous, milk, urine, semen, serum, plasma, sputum, tears, vaginal fluid, or tissue.

3. A rapid diagnostic testing device for rapid diagnostic testing of a blood sample, comprising:
a channeled construct comprising a first side configured to receive at least a portion of the blood sample for rapid separation of blood cells and plasma from the blood sample via a plurality of narrowing channels of the channeled construct, wherein the narrowing channels narrow towards a second side of the channeled construct;
at least one lateral flow unit operatively coupled to the channeled construct, wherein the lateral flow unit comprises:
a sample receiving zone operatively coupled to the channeled construct for receiving at least a portion of the plasma from the second side of the channeled construct, wherein the portion of the plasma comprises an analyte, and wherein the sample receiving zone comprises a first side and a second side;
a conjugate zone disposed adjacent to the first side of the sample receiving zone, wherein the conjugate zone comprises a conjugate particle for binding with the analyte; and
a detection zone disposed adjacent to the second side of the sample receiving zone, wherein the detection zone comprises at least one binding agent for detecting the analyte by capturing the analyte; and
a cassette housing comprising a sample well and a plurality of rib structures extending from the cassette housing into an interior space formed by the cassette housing such that a first rib structure of a first series of the plurality of rib structures positioned relatively closer to the sample well than a second rib structure of the first series of the plurality of rib structures is separated from the lateral flow unit by the channeled construct, wherein the first rib structure directly contacts the first side of the channeled construct, wherein the first side is a top side of the channeled construct, wherein the second rib structure positioned relatively farther from the sample well directly contacts a top surface of the lateral flow unit, and wherein the lateral flow unit is at least partially disposed in the interior space of the cassette housing.

4. The rapid diagnostic testing device of claim 3, wherein the channeled construct is disposed vertically relative to the at least one lateral flow unit.

5. The rapid diagnostic testing device of claim 3, wherein the detection zone comprises a test region and wherein the binding agent is deposited thereon.

6. The rapid diagnostic testing device of claim 3, wherein the binding agent is a primary antibody that binds to the analyte, a labeled primary antibody that binds to the analyte, a secondary antibody that binds to the analyte, or a labeled secondary antibody that binds to the analyte.

7. The rapid diagnostic testing device of claim 3, wherein the conjugate particle comprises a secondary antibody that binds to the analyte.

8. The rapid diagnostic testing device of claim 3, wherein the analyte is selected from a malarial biomarker, an influenza biomarker, a cardiac biomarker, a tumor biomarker, or combinations thereof.

9. The rapid diagnostic testing device of claim 8, wherein the analyte is a malarial biomarker histidine rich protein II (HRP 2).

10. The rapid diagnostic testing device of claim 8, wherein the analyte is a cardiac biomarker CK-MB.

11. The rapid diagnostic testing device of claim 3, wherein the sample receiving zone and the conjugate zone comprises a common substrate.

12. The rapid diagnostic testing device of claim 11, wherein the conjugate particle of the conjugate zone is present at one end of the common substrate and the sample receiving zone is present at another end of the common substrate.

13. The rapid diagnostic testing device of claim 3, wherein the sample receiving zone, the conjugate zone, and the detection zone comprises a common substrate.

14. The rapid diagnostic testing device of claim 3, wherein the lateral flow unit comprises glass fiber, nitrocellulose membrane, quartz, or combinations thereof.

15. The rapid diagnostic testing device of claim 3, wherein the detection zone is present on a nitrocellulose membrane disposed on a separate layer from the sample receiving zone.

16. The rapid diagnostic testing device of claim 3, wherein the lateral flow unit further comprises a buffer reservoir disposed adjacent to the conjugate zone.

17. The rapid diagnostic testing device of claim 16, wherein the buffer reservoir comprises a non-lytic buffer, a buffer with a surfactant concentration of less than about 0.01 mM, or a combination thereof.

18. The rapid diagnostic testing device of claim 3, wherein a volume of the blood sample is in a range from about 25 μL to about 200 μL.

19. The rapid diagnostic testing device of claim 3, wherein the channeled construct comprises a size exclusion separation element that is a porous membrane having a first surface and a second surface, wherein the first surface of the porous membrane is substantially planar with a raised edge surrounding the first surface of the porous membrane.

20. The rapid diagnostic testing device of claim 19, wherein at least a portion of the second surface of the porous membrane of the channeled construct is in contact with the sample receiving zone of the lateral flow unit.

21. The rapid diagnostic testing device of claim 3, wherein the sample well of the cassette housing comprises at least one wall, a first aperture, and a second aperture, and wherein the wall along with the first and second apertures forms a channel, and wherein the second aperture includes a flange.

22. The rapid diagnostic testing device of claim 21, wherein the channeled construct is disposed on the lateral flow unit to form a gap between the second aperture and the channeled construct, such that the flange of the second aperture is positioned to contact the channeled construct.

* * * * *